United States Patent [19]

Ancher et al.

[11] Patent Number: 4,470,993

[45] Date of Patent: Sep. 11, 1984

[54] THERAPEUTICAL USE OF KNOWN 5-AMINOMETHYL OXAZOLIDINE-2-ONE DERIVATIVES

[75] Inventors: Jean-Francois R. Ancher, Rueil Malmaison; Guy R. Bourgery, Colombes; Philippe L. Dostert; Colette A. Douzon, both of Paris; Patrick G. Guerret, Rueil Malmaison; Alain P. Lacour, La Varenne; Michel Langlois, Buc; Margherita Strolin-Benedetti, Paris, all of France

[73] Assignee: Delalande S.A., Courbevoie, France

[21] Appl. No.: 471,920

[22] Filed: Mar. 3, 1983

[30] Foreign Application Priority Data

Mar. 15, 1982 [IT] Italy ................. 20159 A/82

[51] Int. Cl.³ ............................................. A61K 31/42
[52] U.S. Cl. ....................................................... 424/272
[58] Field of Search ........................................ 424/272

[56] References Cited

PUBLICATIONS

"Differential Changes in Monoamine Oxidase A and B Activity in the Aging Rat Brain", Journal of Neurochemistry, 35(5):1026–1032, Nov., by M. STrolin Benedetti and P. E. Keane.

"Biogenic Amines in Human Brain in Normal Aging, Senile Dementia, and Chronic Alcoholism", Ergot Compounds and Brain Function: Neuroendocrine and Neuropsychiatric Aspects, 1980, pp. 295–304, by Arvid Carlsson et al.

"Selective Inhibition of B Type Monoamine Oxidase in the Brain: A Drug Strategy to Improve the Quality of Life in Senescence", Strategy in Drug Research, 1982, p. 107, by J. Knoll.

*Primary Examiner*—Stanley J. Friedman
*Attorney, Agent, or Firm*—Flynn, Thiel, Boutell & Tanis

[57] ABSTRACT

Method of treating the central nervous system troubles such as the Parkinson's disease and the senescence troubles, generally treated by the B type monoamine oxidase inhibitors, which comprises administering internally to a human being requiring such treatment a therapeutically effective amount of N-aryl 5-aminomethyl oxazolidine-2-one derivatives.

7 Claims, No Drawings

THERAPEUTICAL USE OF KNOWN 5-AMINOMETHYL OXAZOLIDINE-2-ONE DERIVATIVES

The present invention concerns a new therapeutical use of known 5-aminomethyl 3-aryl oxazolidine-2-one derivatives and the pharmacologically acceptable organic or mineral acid addition salts thereof.

More precisely, the derivatives employed in the invention have the following formula:

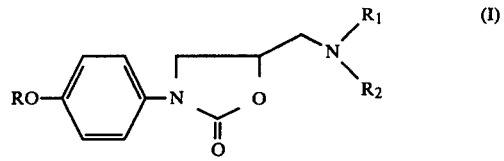

wherein the pair (R, NR$_1$R$_2$) takes on any one of the following values: (n-butyl, N-methylamino), (n-butyl, N,N-dimethylamino), (cyclopentylmethyl, amino), (cyclopentylmethyl, N-methylamino), (3-methyl butyl, amino), (3-methyl butyl, N-methylamino), (cyclohexylmethyl, amino), (cyclohexylmethyl, N-methylamino), (2-cyano ethyl, N,N-dimethylamino), (benzyl, amino), (benzyl, N-methylamino), (m-chlorobenzyl, amino), (m-chlorobenzyl, N-methylamino), (p-fluorobenzyl, amino), (p-fluorobenzyl, N-methylamino), (m-cyanobenzyl, amino), (m-cyanobenzyl, N,N-dimethylamino).

The above derivatives of formula (I) and the pharmacologically acceptable acid addition salts thereof are described in Belgian Pat. No. 876 831 as being able:

to potentiate in mice the generalized trembling caused by intraperitoneal injection of dl-5-hydroxytryptophane, and to oppose to the ptosis observed one hour after an intravenous injection of reserpine, these activities permitting said compounds to be used as potential anti-depressants.

A thorough pharmacological study of these compounds has now revealed that they are also able to inhibit the monoamine oxidase, especially the B type monoamine oxidase.

This activity has been shown ex vivo on rats to which are orally administered the compounds employed in the invention as a 0.5% suspension in methylcellulose. Then the rats are decapitated at various times (30 mn, 1 hour, 2 hours, 4 hours, 8 hours and 24 hours after the administration). The brains are taken up, weighed and homogeneized and the determination of the monoamine oxidase inhibition effect is carried out by using serotonine (specific substrate of the A type monoamine oxidase) and phenylethylamine (specific substrate of B type monoamine oxidase) according to the method described by J. P. KAN and M. STROLIN-BENEDETTI in Life Sciences 26, 2165 (1980).

To illustrate the invention, in table below the results thus obtained are given. (The maximum effect is that observed between 30 minutes and 8 hours).

The acute toxicity is determined orally on mice according to the method described by MILLER and TAINTER in Proc. Soc. Exp. Biol. Med. 57, 261 (1944). The results obtained are also shown in said table.

TABLE

| Tested compound | | Acute toxicity LD 50 (mg/kg/p.o.) | Monoamine oxidase inhibition effect | | | | | |
|---|---|---|---|---|---|---|---|---|
| | | | Dose (mg/kg/ p.o.) | A Type monoamine oxidase | | | B Type monoamine oxidase | | |
| R | NR$_1$R$_2$ | | | max. | 8 hours | 24 hours | max. | 8 hours | 24 hours |
| cyclopentylmethyl | amino | >2000 | 5 | 30 | 9 | 0 | 78 | 17 | 2 |
| benzyl | amino | " | " | 19 | 4 | 4 | 85 | 69 | 45 |
| benzyl | N—methylamino | " | " | 23 | 11 | 10 | 78 | 43 | 31 |
| m-chlorobenzyl | amino | " | " | 30 | 18 | 6 | 88 | 85 | 67 |
| m-chlorobenzyl | N—methylamino | " | " | 28 | 12 | 1 | 83 | 67 | 27 |
| cyclohexylmethyl | amino | " | " | 23 | 13 | 5 | 81 | 60 | 3 |
| cyclohexylmethyl | N—methylamino | " | " | 21 | 17 | 6 | 67 | 42 | 6 |
| 3-methylbutyl | amino | " | " | 29 | 2 | 0 | 69 | 8 | 1 |
| p-fluorobenzyl | N—methylamino | " | " | 44 | 23 | 0 | 85 | 63 | 27 |
| p-fluorobenzyl | amino | " | " | 43 | 20 | 3 | 88 | 82 | 61 |

As shown by the above Table, the difference between the toxic doses and the effective doses are sufficient to allow the derivatives of formula (I) and the salts thereof to be used in therapeutics for their monoamine oxidase inhibition effect. More precisely, they will be used for treating the central nervous system troubles which are generally treated by the B type monoamine oxidase inhibitors; preferably, they will be used possibly in association with L-DOPA, for treating the Parkinson's disease [see for example, Isr. J. Med. Sci. 15, 617 (1979); Adv. in Biochem. Psychopharm. 19, 377; Brit. J. Chem. Pharmacol. 9, 98 (1980)] and for treating the senescence troubles.

The derivatives of formula (I) and their salts will be administered preferably in the form of therapeutical compositions containing at least one of these derivatives or salts in association with a pharmacological acceptable vehicle. Thus, the derivatives and salts can, for example, be administered, orally in the form of pills, tablets or capsules or in the form of solutions or suspensions, at a dose up to 500 mg/day of active ingredient, or parenterally in the form of injectable solute at a dose up to 50 mg/day of active ingredient.

When they are administered orally in the form of pills, tablets or capsules, the latter comprises preferably a vehicle allowing modulation of drug release. As such a vehicle, may be mentioned cellulosic derivatives, vinylic polymers or gums for example. Depending on the vehicle, the pills, tablets or capsules give a prompt or a slow release of the drug.

When the derivatives of formula (I) or their salts are orally administered in the form of a solution or suspension, the latter is preferably an aqueous solution or suspension (vehicle=water) or a partially aqueous solution or suspension (vehicle=water+alcohol, water+glycerine or water+polypropyleneglycol, for example).

When the derivatives of formula (I) or their salts are administered parenterally, they are preferably in the form of injectable solution or suspension freeze drying products.

The embodiments of the invention in which are exclusive property or privilege is claimed are defined as follows:

1. The method of treating Parkinson's disease and senescence ailments that are treated with inhibitors of the activity of B type monoamine oxidase, which comprises administering internally to a human being requiring such treatment a therapeutically effective amount of a compound of formula:

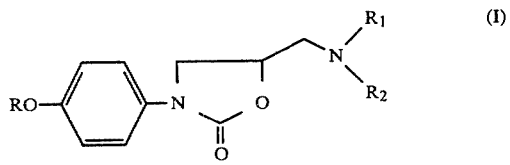

wherein the pair (R, NR$_1$R$_2$) is selected from the group consisting of (n-butyl, N-methylamino), (n-butyl, N,N-dimethylamino), (cyclopentylmethyl, amino), (cyclopentylmethyl, N-methylamino), (3-methyl butyl, amino), (3-methyl butyl, N-methylamino), (cyclohexylmethyl, amino), (cyclohexylmethyl, N-methylamino), (2-cyano ethyl, N,N-dimethylamino), (benzyl, amino), (benzyl, N-methylamino), (m-chlorobenzyl, amino), (m-chlorobenzyl, N-methylamino), (p-fluorobenzyl, amino), (p-fluorobenzyl, N-methylamino), (m-cyanobenzyl, amino) and (m-cyanobenzyl, N,N-dimethylamino),
or a pharmacological acceptable organic or mineral acid addition salt of said derivative of formula (I).

2. The method of claim 1, in which the compound is mixed with a pharmaceutically acceptable carrier.

3. The method of claim 1, in which the compound is administered orally or parenterally.

4. The method of claim 1, in which the drug is administered orally, the therapeutically effective amount being up to 500 mg/day.

5. The method of claim 1, in which the drug is administered parenterally, the therapeutically effective amount being up to 50 mg/day.

6. The method of claim 1, in which NR$_1$R$_2$ is selected from the group consisting of amino and N-methylamino, and R is selected from the group consisting of benzyl, m-chlorobenzyl and p-fluorobenzyl.

7. The method of claim 1, in which NR$_1$R$_2$ is amino and R is selected from the group consisting of m-chlorobenzyl and p-fluorobenzyl.

* * * * *